(12) United States Patent
Glejbol et al.

(10) Patent No.: US 8,197,450 B2
(45) Date of Patent: Jun. 12, 2012

(54) INJECTION DEVICE

(75) Inventors: Kristian Glejbol, Glostrup (DK); Steven Linnebjerg, Skaevinge (DK); Claus Schmidt Moller, Fredensborg (DK); Michael Ejstrup Hansen, Veflinge (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/571,721

(22) Filed: Oct. 1, 2009

(65) Prior Publication Data

US 2010/0016806 A1    Jan. 21, 2010

Related U.S. Application Data

(63) Continuation of application No. 11/911,871, filed as application No. PCT/EP2006/061748 on Apr. 21, 2006, now abandoned.

(60) Provisional application No. 60/676,713, filed on May 2, 2005.

(30) Foreign Application Priority Data

Apr. 24, 2005    (DK) .................................. 2005 00589

(51) Int. Cl.
*A61M 5/00*    (2006.01)
(52) U.S. Cl. ........ 604/211; 604/207; 604/208; 604/209; 604/210
(58) Field of Classification Search ........... 604/207–211
See application file for complete search history.

(56) References Cited

U.S. PATENT DOCUMENTS

| | | |
|---|---|---|
| 854,399 A | 5/1907 | Bridge |
| 2,392,196 A | 2/1946 | Smith |
| 2,956,563 A | 10/1960 | Sarnoff |
| 3,110,310 A | 11/1963 | Cislak |
| 3,115,135 A | 12/1963 | Sarnoff |
| 3,144,178 A | 8/1964 | Sarnoff et al. |
| 3,556,099 A | 1/1971 | Knight et al. |
| 3,729,003 A | 4/1973 | Hurschman |
| 3,880,162 A | 4/1975 | Simmons |
| 3,944,843 A | 3/1976 | Vaz Martins |
| 4,026,288 A | 5/1977 | Costa et al. |
| 4,231,368 A | 11/1980 | Becker |
| 4,275,727 A | 6/1981 | Keeri-Szanto |
| 4,277,227 A | 7/1981 | Jenkins |

(Continued)

FOREIGN PATENT DOCUMENTS

AU    2003232576    1/2004

(Continued)

OTHER PUBLICATIONS

Answer in *Novo Nordisk A/S v. Sanofi-Aventis U.S. LLC and Sanofi-Aventis* downloaded from Pacer on Feb. 29, 2008.

(Continued)

*Primary Examiner* — Kevin C Sirmons
*Assistant Examiner* — Imani Hayman
(74) *Attorney, Agent, or Firm* — Marc A. Began

(57) ABSTRACT

An injection device for injection of set doses of medicine from a cartridge has a nut that is screwed up along a threaded piston rod during a dose setting operation. The nut is screwed along the piston rod by rotating a dose setting member. A rotational coupling mechanism includes an axially displaceable coupling member which is rotated as a function of axial displacement. During dose setting, the nut is allowed to rotate relative to the coupling member. During injection, the coupling member is rotationally locked to the nut. This provides a dose setting and injection mechanism wherein the nut member is both rotated during dose setting and during injection.

21 Claims, 5 Drawing Sheets

U.S. PATENT DOCUMENTS

| | | |
|---|---|---|
| 4,298,000 A | 11/1981 | Thill et al. |
| 4,300,554 A | 11/1981 | Hessberg et al. |
| 4,313,439 A | 2/1982 | Babb et al. |
| 4,314,556 A | 2/1982 | Ma |
| 4,368,731 A | 1/1983 | Schramm |
| RE31,315 E | 7/1983 | Jenkins et al. |
| 4,393,723 A | 7/1983 | Brand |
| 4,430,079 A | 2/1984 | Thill et al. |
| 4,465,478 A | 8/1984 | Sabelman et al. |
| 4,470,317 A | 9/1984 | Sabloewski et al. |
| 4,493,704 A | 1/1985 | Beard et al. |
| 4,498,904 A | 2/1985 | Turner et al. |
| 4,515,584 A | 5/1985 | Hiroshi et al. |
| 4,568,335 A | 2/1986 | Updike et al. |
| 4,585,439 A | 4/1986 | Michel |
| 4,634,431 A | 1/1987 | Whitney et al. |
| 4,676,122 A | 6/1987 | Szabo et al. |
| 4,749,109 A | 6/1988 | Kamen |
| 4,812,724 A | 3/1989 | Langer et al. |
| 4,833,379 A | 5/1989 | Kaibel et al. |
| 4,838,860 A | 6/1989 | Groshong et al. |
| 4,865,591 A | 9/1989 | Sams |
| 4,871,351 A | 10/1989 | Feingold |
| 4,883,472 A | 11/1989 | Michel |
| 4,893,291 A | 1/1990 | Bick et al. |
| 4,898,578 A | 2/1990 | Rubalcaba |
| 4,919,596 A | 4/1990 | Slate et al. |
| 4,936,833 A | 6/1990 | Sams |
| 4,950,246 A | 8/1990 | Muller |
| 4,973,318 A | 11/1990 | Holm |
| 4,988,337 A | 1/1991 | Ito |
| 4,994,033 A | 2/1991 | Shockey et al. |
| 5,000,744 A | 3/1991 | Hoffman et al. |
| 5,002,537 A | 3/1991 | Hoffman et al. |
| 5,064,098 A | 11/1991 | Hutter et al. |
| 5,078,698 A | 1/1992 | Stiehl et al. |
| 5,104,388 A | 4/1992 | Quackenbush |
| 5,112,317 A | 5/1992 | Michel |
| 5,113,869 A | 5/1992 | Nappholz et al. |
| 5,114,406 A | 5/1992 | Gabriel et al. |
| 5,135,485 A | 8/1992 | Cohen et al. |
| 5,163,904 A | 11/1992 | Lampropoulos et al. |
| 5,176,646 A | 1/1993 | Kuroda |
| 5,207,752 A | 5/1993 | Sorenson et al. |
| 5,221,268 A | 6/1993 | Barton et al. |
| 5,226,342 A | 7/1993 | Panin |
| 5,226,895 A | 7/1993 | Harris |
| 5,226,896 A | 7/1993 | Harris |
| 5,244,461 A | 9/1993 | Derlien |
| 5,244,465 A | 9/1993 | Michel |
| 5,246,417 A | 9/1993 | Haak et al. |
| 5,257,987 A | 11/1993 | Athayde et al. |
| 5,271,527 A | 12/1993 | Haber et al. |
| 5,279,585 A | 1/1994 | Balkwill |
| 5,279,586 A | 1/1994 | Balkwill |
| 5,281,198 A | 1/1994 | Haber et al. |
| 5,284,480 A | 2/1994 | Porter et al. |
| 5,292,976 A | 3/1994 | Dessau et al. |
| 5,295,976 A | 3/1994 | Harris |
| 5,304,152 A | 4/1994 | Sams |
| 5,308,340 A | 5/1994 | Harris |
| 5,314,412 A | 5/1994 | Rex |
| 5,318,540 A | 6/1994 | Athayde et al. |
| 5,320,609 A | 6/1994 | Haber et al. |
| 5,331,954 A | 7/1994 | Rex et al. |
| 5,368,572 A | 11/1994 | Shirota |
| 5,370,629 A | 12/1994 | Michel et al. |
| 5,378,233 A | 1/1995 | Haber et al. |
| 5,383,856 A | 1/1995 | Bersin |
| 5,383,865 A | 1/1995 | Michel |
| 5,440,976 A | 8/1995 | Giuliano et al. |
| 5,445,606 A | 8/1995 | Haak et al. |
| 5,447,150 A | 9/1995 | Bacon |
| 5,478,316 A | 12/1995 | Bitdinger et al. |
| 5,480,387 A | 1/1996 | Gabriel et al. |
| 5,492,534 A | 2/1996 | Athayde et al. |
| 5,496,286 A | 3/1996 | Stiehl et al. |
| 5,505,697 A | 4/1996 | McKinnon, Jr. et al. |
| 5,505,704 A | 4/1996 | Pawelka et al. |
| 5,536,249 A | 7/1996 | Castellano et al. |
| 5,546,932 A | 8/1996 | Galli |
| 5,549,575 A | 8/1996 | Giambattista |
| 5,573,729 A | 11/1996 | Belgardt et al. |
| 5,582,598 A | 12/1996 | Chanoch |
| 5,584,815 A | 12/1996 | Pawelka et al. |
| 5,591,136 A | 1/1997 | Gabriel |
| 5,593,390 A | 1/1997 | Castellano et al. |
| 5,599,314 A | 2/1997 | Neill |
| 5,611,783 A | 3/1997 | Mikkelsen |
| 5,611,784 A | 3/1997 | Barresi et al. |
| 5,626,566 A | 5/1997 | Petersen et al. |
| 5,628,309 A | 5/1997 | Brown |
| 5,637,095 A | 6/1997 | Nason et al. |
| 5,645,052 A | 7/1997 | Kersey |
| 5,662,612 A | 9/1997 | Niehoff |
| 5,674,204 A | 10/1997 | Chanoch |
| 5,679,111 A | 10/1997 | Hertman et al. |
| 5,681,285 A | 10/1997 | Ford et al. |
| 5,685,864 A | 11/1997 | Shanley et al. |
| 5,688,251 A | 11/1997 | Chanoch |
| 5,709,662 A | 1/1998 | Olive et al. |
| 5,716,990 A | 2/1998 | Bagshawe et al. |
| 5,720,733 A | 2/1998 | Brown |
| 5,725,508 A | 3/1998 | Chanoch et al. |
| 5,728,074 A | 3/1998 | Castellano et al. |
| 5,728,559 A | 3/1998 | Nilsson et al. |
| 5,741,211 A | 4/1998 | Renirie et al. |
| 5,743,889 A | 4/1998 | Sams |
| 5,755,692 A | 5/1998 | Manicom |
| 5,782,633 A | 7/1998 | Mühlbauer |
| 5,807,334 A | 9/1998 | Hodosh et al. |
| 5,814,022 A | 9/1998 | Antanavich et al. |
| 5,820,602 A | 10/1998 | Kovelman et al. |
| 5,823,998 A | 10/1998 | Yamagata |
| 5,827,232 A | 10/1998 | Chanoch |
| 5,830,194 A | 11/1998 | Anwar et al. |
| 5,843,036 A | 12/1998 | Olive et al. |
| 5,879,360 A | 3/1999 | Crankshaw |
| 5,879,630 A | 3/1999 | Lescouzeres et al. |
| 5,882,718 A | 3/1999 | Pommer et al. |
| 5,898,028 A | 4/1999 | Jensen et al. |
| 5,921,966 A | 7/1999 | Bendek et al. |
| 5,928,201 A | 7/1999 | Poulsen et al. |
| 5,933,671 A | 8/1999 | Stephany et al. |
| 5,938,642 A | 8/1999 | Burroughs et al. |
| 5,947,934 A | 9/1999 | Hansen et al. |
| 5,951,530 A | 9/1999 | Steengaard et al. |
| 5,954,689 A | 9/1999 | Poulsen |
| 5,954,700 A | 9/1999 | Kovelman |
| 5,957,889 A | 9/1999 | Poulsen et al. |
| 5,961,496 A | 10/1999 | Nielsen et al. |
| 5,971,963 A | 10/1999 | Choi |
| 5,980,491 A | 11/1999 | Hansen |
| 5,984,900 A | 11/1999 | Mikkelson |
| 5,989,221 A | 11/1999 | Hjertman et al. |
| 5,998,989 A | 12/1999 | Lohberg |
| 6,003,736 A | 12/1999 | Ljunggren |
| 6,004,297 A | 12/1999 | Steenfeldt-Jensen |
| 6,010,485 A | 1/2000 | Buch-Rasmussen et al. |
| 6,033,376 A | 3/2000 | Rockley |
| 6,033,377 A | 3/2000 | Rasmussen et al. |
| 6,036,675 A | 3/2000 | Thorne et al. |
| 6,048,336 A | 4/2000 | Gabriel |
| 6,074,372 A | 6/2000 | Hansen et al. |
| 6,083,197 A | 7/2000 | Umbaugh |
| 6,086,567 A | 7/2000 | Kirchhofer et al. |
| 6,096,010 A | 8/2000 | Walters et al. |
| 6,110,148 A | 8/2000 | Brown et al. |
| 6,110,149 A | 8/2000 | Klitgaard et al. |
| 6,129,080 A | 10/2000 | Pitcher et al. |
| 6,146,361 A | 11/2000 | DiBiasi et al. |
| 6,159,161 A | 12/2000 | Hodosh |
| 6,161,364 A | 12/2000 | Kolberg |
| 6,193,698 B1 | 2/2001 | Kirchhofer et al. |
| 6,221,046 B1 | 4/2001 | Burroughs et al. |
| 6,221,053 B1 | 4/2001 | Walters |
| 6,231,540 B1 | 5/2001 | Smedegaard |

| | | |
|---|---|---|
| 6,235,004 B1 | 5/2001 | Steenfeldt-Jensen |
| 6,245,046 B1 | 6/2001 | Sibbitt |
| 6,248,090 B1 | 6/2001 | Jensen et al. |
| 6,248,095 B1 | 6/2001 | Giambatista et al. |
| 6,258,062 B1 | 7/2001 | Thielen et al. |
| 6,268,722 B1 | 7/2001 | Kogure et al. |
| 6,269,340 B1 | 7/2001 | Ford et al. |
| 6,277,097 B1 | 8/2001 | Mikkelsen et al. |
| 6,277,098 B1 | 8/2001 | Klitmose et al. |
| 6,281,225 B1 | 8/2001 | Hearst et al. |
| 6,283,941 B1 | 9/2001 | Schoenfeld et al. |
| 6,287,283 B1 | 9/2001 | Ljunggreen et al. |
| 6,302,869 B1 | 10/2001 | Klitgaard |
| 6,312,413 B1 | 11/2001 | Jensen et al. |
| 6,340,357 B1 | 1/2002 | Poulsen et al. |
| 6,364,860 B1 | 4/2002 | Steck et al. |
| 6,379,339 B1 | 4/2002 | Klitgaard et al. |
| 6,383,167 B2 | 5/2002 | Kirchhofer et al. |
| 6,391,005 B1 | 5/2002 | Lum et al. |
| 6,419,661 B1 | 7/2002 | Kuhr et al. |
| 6,514,230 B1 | 2/2003 | Munk et al. |
| 6,537,251 B2 | 3/2003 | Klitmose |
| 6,547,755 B1 | 4/2003 | Lippe et al. |
| 6,547,763 B2 | 4/2003 | Steenfeldt-Jensen |
| 6,547,764 B2 | 4/2003 | Larsen et al. |
| 6,562,011 B1 | 5/2003 | Buch-Rasmussen et al. |
| 6,569,126 B1 | 5/2003 | Poulsen et al. |
| 6,582,404 B1 | 6/2003 | Klitgaard et al. |
| 6,585,698 B1 | 7/2003 | Packman et al. |
| 6,599,272 B1 | 7/2003 | Hjertman et al. |
| 6,605,067 B1 | 8/2003 | Larsen |
| 6,613,019 B2 | 9/2003 | Munk |
| 6,663,602 B2 | 12/2003 | Moller |
| 6,666,849 B1 | 12/2003 | Marshall et al. |
| 6,673,033 B1 | 1/2004 | Sciulli et al. |
| 6,692,472 B2 | 2/2004 | Hansen et al. |
| 6,699,224 B2 | 3/2004 | Kirchhofer et al. |
| 6,716,198 B2 | 4/2004 | Larsen |
| 6,726,661 B2 | 4/2004 | Munk et al. |
| 6,752,798 B2 | 6/2004 | McWethy et al. |
| 6,770,288 B2 | 8/2004 | Duirs |
| 6,796,970 B1 | 9/2004 | Klitmose et al. |
| 6,852,404 B2 | 2/2005 | Kuwajima et al. |
| 6,887,238 B2 | 5/2005 | Jahns et al. |
| 6,893,415 B2 | 5/2005 | Madsen et al. |
| 6,899,698 B2 | 5/2005 | Sams |
| 6,899,699 B2 | 5/2005 | Enggaard |
| 6,945,961 B2 | 9/2005 | Miller et al. |
| 7,008,399 B2 | 3/2006 | Larsen et al. |
| 7,080,936 B1 | 7/2006 | Simpson |
| 7,090,662 B2 | 8/2006 | Wimpenny et al. |
| 7,094,221 B2 | 8/2006 | Veasey et al. |
| 7,104,972 B2 | 9/2006 | Moller et al. |
| 7,133,329 B2 | 11/2006 | Skyggebjerg et al. |
| 7,175,055 B2 | 2/2007 | Hansen et al. |
| 7,195,609 B2 | 3/2007 | Huegli |
| 7,195,616 B2 | 3/2007 | Diller et al. |
| 7,241,278 B2 | 7/2007 | Moller |
| 7,500,966 B2 | 3/2009 | Hommann |
| 7,678,084 B2 | 3/2010 | Judson et al. |
| 7,704,238 B2 | 4/2010 | Diller et al. |
| 2001/0034506 A1 | 10/2001 | Hirschman et al. |
| 2001/0053893 A1 | 12/2001 | Larsen |
| 2002/0002326 A1 | 1/2002 | Causey, III et al. |
| 2002/0007154 A1 | 1/2002 | Hansen et al. |
| 2002/0016571 A1 | 2/2002 | Kirchhofer et al. |
| 2002/0020654 A1 | 2/2002 | Eilersen |
| 2002/0049415 A1 | 4/2002 | Fukuda |
| 2002/0052578 A1 | 5/2002 | Moller |
| 2002/0077852 A1 | 6/2002 | Ford et al. |
| 2002/0107486 A1 | 8/2002 | Munk |
| 2002/0120235 A1 | 8/2002 | Enggaard |
| 2002/0165500 A1 | 11/2002 | Bechtold et al. |
| 2002/0173752 A1 | 11/2002 | Polzin |
| 2002/0188250 A1 | 12/2002 | Landau et al. |
| 2003/0009133 A1 | 1/2003 | Ramey |
| 2003/0039679 A1 | 2/2003 | Duirs |
| 2003/0073954 A1 | 4/2003 | Moberg et al. |
| 2003/0114800 A1 | 6/2003 | Veasey et al. |
| 2003/0172924 A1 | 9/2003 | Staniforth et al. |
| 2003/0176871 A1 | 9/2003 | Pavlov et al. |
| 2003/0216663 A1 | 11/2003 | Willuhn et al. |
| 2003/0233075 A1 | 12/2003 | Huegli et al. |
| 2004/0010204 A1 | 1/2004 | Weber et al. |
| 2004/0024361 A1 | 2/2004 | Fago |
| 2004/0051368 A1 | 3/2004 | Caputo et al. |
| 2004/0059299 A1 | 3/2004 | Moller |
| 2004/0097879 A1 | 5/2004 | Woolston |
| 2004/0108339 A1 | 6/2004 | Hansen et al. |
| 2004/0158304 A1 | 8/2004 | Cory et al. |
| 2004/0171983 A1 | 9/2004 | Sparks et al. |
| 2004/0186431 A1 | 9/2004 | Graf et al. |
| 2004/0207385 A1 | 10/2004 | Gafner et al. |
| 2004/0210199 A1 | 10/2004 | Atterbury et al. |
| 2004/0230157 A1 | 11/2004 | Perry et al. |
| 2004/0236282 A1 | 11/2004 | Braithwaite |
| 2004/0249348 A1 | 12/2004 | Wimpenny et al. |
| 2004/0260247 A1 | 12/2004 | Veasey et al. |
| 2004/0267207 A1 | 12/2004 | Veasey et al. |
| 2004/0267208 A1 | 12/2004 | Veasey et al. |
| 2005/0004529 A1 | 1/2005 | Veasey et al. |
| 2005/0019400 A1 | 1/2005 | Deveney et al. |
| 2005/0033244 A1 | 2/2005 | Veasey et al. |
| 2005/0055011 A1 | 3/2005 | Enggaard |
| 2005/0197625 A1 | 9/2005 | Haueter et al. |
| 2005/0205083 A1 | 9/2005 | Staniforth et al. |
| 2005/0209570 A1 | 9/2005 | Møller |
| 2005/0268915 A1 | 12/2005 | Wassenaar et al. |
| 2006/0118612 A1 | 6/2006 | Christoffersen et al. |
| 2006/0258988 A1 | 11/2006 | Keitel et al. |
| 2006/0264838 A1 | 11/2006 | Volckmann |
| 2007/0093761 A1 | 4/2007 | Veasey et al. |
| 2007/0244445 A1 | 10/2007 | Moller |
| 2008/0065026 A1 | 3/2008 | Moller |
| 2008/0221530 A1 | 9/2008 | Glejbol et al. |
| 2008/0281275 A1 | 11/2008 | Moller |
| 2009/0043264 A1 | 2/2009 | Glejbol et al. |
| 2009/0062748 A1 | 3/2009 | Moller et al. |

FOREIGN PATENT DOCUMENTS

| | | |
|---|---|---|
| CA | 2359375 | 7/2000 |
| DE | 3048135 | 7/1982 |
| DE | 3236374 | 4/1984 |
| DE | 3609555 | 9/1987 |
| DE | 3609555 A1 | 9/1987 |
| DE | 3638984 | 5/1988 |
| DE | 3923079 | 1/1991 |
| DE | 4223958 | 1/1993 |
| DE | 4419235 | 12/1995 |
| DE | 19503230 | 8/1996 |
| DE | 29513214 | 2/1997 |
| DE | 19723647 | 12/1998 |
| DE | 19838760 | 4/2000 |
| DE | 29907880 | 9/2000 |
| DE | 10103287 | 8/2001 |
| DE | 10201875 | 5/2003 |
| DE | 10229122 | 2/2004 |
| DE | 20317377 | 4/2005 |
| DE | 102004046003 | 3/2006 |
| DK | 200100240 | 2/2001 |
| DK | 2005/00116 | 6/2005 |
| EP | 15617 | 9/1980 |
| EP | 017318 | 10/1980 |
| EP | 0064858 | 11/1982 |
| EP | 327810 | 8/1989 |
| EP | 327910 | 8/1989 |
| EP | 338806 | 10/1989 |
| EP | 0362484 | 4/1990 |
| EP | 387854 | 9/1990 |
| EP | 422482 | 4/1991 |
| EP | 454331 | 10/1991 |
| EP | 0327 910 B1 | 4/1992 |
| EP | 498737 | 8/1992 |
| EP | 879610 | 8/1992 |
| EP | 0513128 | 11/1992 |
| EP | 608343 | 4/1993 |
| EP | 554996 | 8/1993 |
| EP | 594349 | 4/1994 |

| | | | | | |
|---|---|---|---|---|---|
| EP | 615762 | 9/1994 | RU | 2091087 | 9/1997 |
| EP | 513128 | 7/1995 | RU | 2212254 | 9/2003 |
| EP | 0673482 | 9/1995 | WO | WO8502256 | 5/1985 |
| EP | 679440 | 11/1995 | WO | 8702895 A1 | 5/1987 |
| EP | 702970 | 3/1996 | WO | WO 87/02895 | 5/1987 |
| EP | 1000631 | 10/1997 | WO | 8907463 | 8/1989 |
| EP | 554995 | 12/1997 | WO | WO 89/07463 | 8/1989 |
| EP | 295075 | 12/1998 | WO | 90/09202 | 8/1990 |
| EP | 897728 | 2/1999 | WO | WO 90/09202 | 8/1990 |
| EP | 0937 471 A2 | 8/1999 | WO | 9110460 | 7/1991 |
| EP | 0937472 | 8/1999 | WO | WO 91/10460 | 7/1991 |
| EP | 0937476 | 8/1999 | WO | WO91/10677 | 7/1991 |
| EP | 1003581 | 8/1999 | WO | WO 91/14467 | 10/1991 |
| EP | 956873 A2 | 11/1999 | WO | WO9301573 | 1/1993 |
| EP | 0937 471 A3 | 2/2000 | WO | WO 9303780 | 3/1993 |
| EP | 1351732 | 1/2001 | WO | WO 93/07922 | 4/1993 |
| EP | 1074273 | 2/2001 | WO | WO 9412228 | 6/1994 |
| EP | 10074273 | 2/2001 | WO | WO9524233 | 9/1995 |
| EP | 1095668 | 5/2001 | WO | WO 96/07443 | 3/1996 |
| EP | 0747391 | 3/2004 | WO | WO 96/26754 | 9/1996 |
| EP | 1462134 | 9/2004 | WO | WO 96/32973 | 10/1996 |
| EP | 937476 | 1/2005 | WO | WO 96/38190 | 12/1996 |
| EP | 1541185 | 6/2005 | WO | WO 97/07841 | 3/1997 |
| EP | 1557163 | 7/2005 | WO | WO 9710865 | 3/1997 |
| EP | 1557189 | 7/2005 | WO | WO9730742 | 8/1997 |
| EP | 1 568 389 | 8/2005 | WO | WO97/34919 | 9/1997 |
| EP | 0937 471 B1 | 9/2005 | WO | WO 97/36626 | 10/1997 |
| EP | 1304129 | 11/2005 | WO | WO 98/10813 | 3/1998 |
| EP | 1610848 | 1/2006 | WO | WO 98/56436 | 12/1998 |
| EP | 1645301 | 4/2006 | WO | WO 98/57688 | 12/1998 |
| EP | 1723977 | 11/2006 | WO | WO9907425 | 2/1999 |
| EP | 1728529 | 12/2006 | WO | WO 99/16487 | 4/1999 |
| EP | 1782853 | 5/2007 | WO | wo9915214 | 4/1999 |
| EP | 1819382 | 8/2007 | WO | WO 9916487 | 4/1999 |
| EP | 2000161 | 12/2008 | WO | WO 9921598 | 5/1999 |
| EP | 2019701 A1 | 2/2009 | WO | WO 99/38554 | 8/1999 |
| FR | 2583291 | 12/1986 | WO | WO99/38554 | 8/1999 |
| FR | 2622457 | 5/1989 | WO | WO9948546 | 9/1999 |
| FR | 2697434 | 5/1994 | WO | WO9965548 | 12/1999 |
| FR | 2740345 | 4/1997 | WO | WO0037129 | 6/2000 |
| FR | 2767479 | 2/1999 | WO | WO 00/51668 | 9/2000 |
| FR | 2857654 | 1/2005 | WO | 01/19434 A1 | 3/2001 |
| GB | 664044 | 1/1952 | WO | WO 01/19434 | 3/2001 |
| GB | 2091107 | 7/1982 | WO | WO0126710 | 4/2001 |
| GB | 2153445 | 8/1985 | WO | WO 01/30425 | 5/2001 |
| GB | 2229497 | 9/1990 | WO | WO 0130425 | 5/2001 |
| GB | 2309644 | 8/1997 | WO | WO0172361 | 10/2001 |
| GB | 0007071.4 | 3/2000 | WO | 0195959 A1 | 12/2001 |
| IN | 165367 | 3/1986 | WO | WO 01/95959 | 12/2001 |
| JP | 56-163486 | 12/1981 | WO | WO0205876 | 1/2002 |
| JP | 57-000033 | 1/1982 | WO | WO0224257 | 3/2002 |
| JP | 01-100495 | 4/1989 | WO | 02/053214 | 7/2002 |
| JP | 01-035671 | 6/1989 | WO | WO 02/053214 | 7/2002 |
| JP | 02071758 A | 3/1990 | WO | WO02064196 | 8/2002 |
| JP | 02-126184 | 5/1990 | WO | 02/076537 | 10/2002 |
| JP | 02-182267 | 7/1990 | WO | 02076536 | 10/2002 |
| JP | 4-224764 | 8/1992 | WO | WO 02/076535 | 10/2002 |
| JP | 04256757 A | 9/1992 | WO | WO 02/076536 | 10/2002 |
| JP | 4-507059 | 12/1992 | WO | 02/092153 A2 | 11/2002 |
| JP | 05-337179 | 12/1993 | WO | WO 02/092153 | 11/2002 |
| JP | 06-055644 | 1/1994 | WO | WO03057283 | 7/2003 |
| JP | 7-500039 | 3/1994 | WO | WO03063680 | 8/2003 |
| JP | 06-034825 | 10/1994 | WO | WO9733638 | 9/2003 |
| JP | 06-296691 | 10/1994 | WO | WO 03/080160 | 10/2003 |
| JP | 7-500039 | 1/1995 | WO | WO03099357 | 12/2003 |
| JP | 7-502678 | 3/1995 | WO | WO 2004/002556 | 1/2004 |
| JP | 09166474 | 6/1997 | WO | WO 2004/007002 | 1/2004 |
| JP | 11511364 | 10/1999 | WO | WO 2004004825 | 1/2004 |
| JP | 3017167 | 11/1999 | WO | WO 2004/024218 | 3/2004 |
| JP | 200237308 | 9/2000 | WO | WO 2004/028598 | 4/2004 |
| JP | 2000237308 | 9/2000 | WO | WO 2004/035113 | 4/2004 |
| JP | 2003284777 | 10/2003 | WO | WO 2004/078239 | 9/2004 |
| JP | 2004-503303 | 2/2004 | WO | WO 2004/078240 | 9/2004 |
| JP | 2004-516895 | 6/2004 | WO | WO 2004/078241 | 9/2004 |
| JP | 2005536300 A | 12/2005 | WO | WO 2004078242 | 9/2004 |
| JP | 2006250582 | 9/2006 | WO | WO2004080306 | 9/2004 |
| JP | 2007-509662 | 4/2007 | WO | WO2004084795 | 10/2004 |
| RE | 31315 | 7/1983 | WO | WO2004095379 | 11/2004 |
| RU | 2111019 | 5/1997 | WO | 2005018721 | 3/2005 |

| | | |
|---|---|---|
| WO | WO 2005018721 | 3/2005 |
| WO | 2005037352 | 4/2005 |
| WO | WO 2005037352 | 4/2005 |
| WO | WO 2005/046770 | 5/2005 |
| WO | WO 20057046770 | 5/2005 |
| WO | WO2005089835 | 9/2005 |
| WO | 2005097233 | 10/2005 |
| WO | 2005097240 | 10/2005 |
| WO | WO 2006039930 | 4/2006 |
| WO | WO 2006/045528 | 5/2006 |
| WO | WO 2006/045529 | 5/2006 |
| WO | WO2006045425 | 5/2006 |
| WO | WO2006045525 | 5/2006 |
| WO | WO 2006/069454 | 7/2006 |
| WO | WO2006076921 | 7/2006 |
| WO | WO2006116997 | 11/2006 |
| WO | WO 2006/128794 | 12/2006 |
| WO | WO 2007/030957 | 3/2007 |
| WO | WO2007041843 | 4/2007 |
| WO | WO2007107558 | 9/2007 |
| WO | WO2007107561 | 9/2007 |
| WO | WO 2007/134954 | 11/2007 |
| WO | WO 2008/037801 | 4/2008 |
| WO | WO2008057223 | 5/2008 |

OTHER PUBLICATIONS

Chia Kai Su et al, Process Biochemistry, 2006, vol. 41, Part 2, pp. 257-263.
Complaint in *Novo Nordiks A/S v. Sanofi-Aventis U.S. LLC and Sanofi-Aventis* downloaded from Pacer on Feb. 29, 2008.
Declaration of Benard Sams in *Novo Nordisk A/S v. Sanofi-Aventis U.S. LLC and Sanofi-Aventis* downloaded from Pacer on Feb. 29, 2008.
Dennison, Clive et al, Protein Expression and Purification, 2004, vol. 11, Part 2, pp. 149-161.
English Language Abstract of French Patent No. 2697434, published on May 16, 1994 obtained from Derwent Patent Database.
English Language Abstract of French Patent No. 2767479, published on Feb. 26, 1999 obtained from Derwent Patent Database.
English Language Abstract of German Patent No. 3048135, published on Jul. 15, 1982 obtained from Derwent Patent Database.
Fransson et al, Pharmaceutical Research, 1997, vol. 14, Part 5, pp. 606-612.
International Search Report and Written Opinion issued in connection with counterpart PCT Application No. PCT/EP2006/061747, mailed Sep. 29, 2006.
International Search Report and Written Opinion issued in connection with counterpart PCT Application No. PCT/EP2006/061747 mailed Sep. 29, 2006.
Leonil et al, Enzyme and Microbiol Technology, 1994, vol. 16, Part 7, pp. 591-595.
Machine translation of EP679440TX.
Machine translation of FR2583291TX.
Machine translation of FR2767479TX.
Machine translation of FR2697434TX.
Machine translation of DE3048135TX.
Machine translation of DE3609555TX.
English Abstract of JP57-000033.
English Abstract of JP06-296691.
English Abstract of JP64-035671.
English Abstract of JP06-055644.
English Abstract of JP06-034825.
May 17, 2002 Office Action in U.S. Appl. No. 09/768,760 and accompanying 892 and 1149 forms.
Opinion of US District Court for the District of NJ (Docket No. 3:07-cv-03206-MLC-JJH in *Novo Nordisk A/S v. Sanofi-Aventis U.S. LLC and Sanofi-Aventis* Denying motion of a preliminary injunction entered Feb. 20, 2008.
Print-out of file history of U.S. Appl. No. 10/610,926 which is owned by the same assignee as U.S. Appl. No. 11/765,789.
Paule, B.J.A. et al, Protein Expression and Purification, 2004, vol. 34, Part 2, pp. 311-316.
Search Report issued in connection with counterpart Danish Application No. PA 2005 00588, mailed Feb. 13, 2006.
Reissue U.S. Appl. No. 10/442,855 File History.
Reissue U.S. Appl. No. 10/960,900 File History.
Reissue U.S. Appl. No. 11/121,331 File History.
Reissue U.S. Appl. No. 11/640,610 File History.
Written Opinion issued in connection with counterpart PCT Application No. PCT/EP2006/061747, mailed Nov. 8, 2006.
Search Report issued in connection with counterpart Danish Application No. PA 2005 00589, mailed Feb. 16, 2006.
International Search Report and Written Opinion issued in connection with counterpart PCT Application No. PCT/EP2006/061748, mailed Aug. 10, 2006.
Written Opinion issued in connection with counterpart PCT Application No. PCT/EP2006/061748, mailed Nov. 8, 2006.
Office Action Mailed Mar. 17, 1999 in U.S. Appl. No. 08/973,109, filed Jun. 3, 1996 by Klitmose.
Notice of Allowance Mailed Oct. 25, 1999 in U.S. Appl. No. 08/973,109, filed Jun. 3, 1996 by Klitmose.
Office Action Mailed Apr. 26, 1999 in U.S. Appl. No. 09/090,144, filed Jun. 4, 1998 by Klitmose.
Final Action Mailed Dec. 20, 1999 in U.S. Appl. No. 09/090,114, filed Jun. 4, 1998 by Klitmose.
Notice of Allowance Mailed Apr. 6, 2004 in U.S. Appl. No. 09/090,144, filed Jun. 4, 1998 by Klitmose.
Non-Final Office Action Mailed Aug. 27, 2002 in U.S. Appl. No. 09/882,536, filed Jun. 14, 2001 by Moller et al.
Notice of Allowance Mailed Jun. 17, 2003 in U.S. Appl. No. 09/882,536, filed Jun. 4, 2001 by Moller et al.
Notice of Allowance Mailed on Apr. 23, 2007 in U.S. Appl. No. 10/667,040, filed Sep. 22, 2003 by Moller et al.
Office Action Mailed Mar. 17, 2008 in U.S. Appl. No. 11/122,289, filed May 4, 2005 by Moller et al.
Non-Final Rejection Mailed on Dec. 15, 2008 in U.S. Appl. No. 11/122,289, filed May 4, 2005 by Moller et al.
Final Action Mailed Nov. 5, 2009. In U.S. Appl. No. 11/122,289, filed May 4, 2005 by Moller et al.
Advisory Action Mailed on Mar. 25, 2010 in U.S. Appl. No. 11/122,289, filed May 4, 2005 by Moller et al.
Final Action Mailed on Nov. 5, 2009 in U.S. Appl. No. 11/765,789, filed Jun. 20, 2007 by Moller et al.
Office Action Mailed on Dec. 17, 2008 in U.S. Appl. No. 11/765,789, filed Jun. 20, 2007 by Moller et al.
Office Action Mailed on Mar. 14, 2008 in U.S. Appl. No. 11/765,789, filed Jun. 20, 2007 by Moller et al.
Final Action Mailed on Jan. 15, 2010 in U.S. Appl. No. 11/930,926, filed Oct. 31, 2007 by Moller et al.
Office Action Mailed From the USPTO on Apr. 2, 2009 in U.S. Appl. No. 11/930,926, filed Oct. 31, 2007 by Moller et al.
Final Office Action Mailed on Jan. 15, 2010 in U.S. Appl. No. 11/931,010, filed Oct. 31, 2007 by Moller et al.
Office Action Mailed on Apr. 2, 2009 in U.S. Appl. No. 11/931,010, filed Oct. 31, 2007 by Moller et al.
Office Action Mailed on Sep. 15, 2004 in U.S. Appl. No. 10/646,295, filed Aug. 22, 2003 by Iiansen et al.
Final Office Action Mailed on Feb. 8, 2005 in U.S. Appl. No. 10/646,295, filed Aug. 22, 2003 by Hansen et al.
Advisory Action Mailed Jul. 1, 2005 in U.S. Appl. No. 10/646,295, filed Aug. 22, 2003 by Hansen et al.
Office Action Mailed on Aug. 29, 2005 in U.S. Appl. No. 10/646,295, filed Aug. 22, 2003 by Hansen et al.
Final Office Action Mailed on Apr. 14, 2006 in U.S. Appl. No. 10/646,295, filed Aug. 22, 2003 by Hansen et al.
Notice of Allowance Mailed on Sep. 26, 2006 in U.S. Appl. No. 10/646,295, filed Aug. 22, 2003 by Hansen et al.
Office Action Mailed on Jan. 8, 2009 in U.S. Appl. No. 11/911,869, filed Oct. 18, 2007 by Glejbol et al.
Final Office Action Mailed on Sep. 29, 2009 in U.S. Appl. No. 11/911,869, filed Oct. 18, 2007 by Glejbol et al.
Abandonment Mailed on Oct. 8, 2009 in U.S. Appl. No. 11/911,869, filed Oct. 18, 2007 by Glejbol et al.
Office Action Mailed on Apr. 1, 2009 in U.S. Appl. No. 11/911,871, filed Oct. 18, 2007 by Glejbol et al.
Abandonment Mailed on Nov. 6, 2009 in U.S. Appl. No. 11/911,871, filed Oct. 18, 2007 by Glejbol et al.

Office Action Mailed Jul. 20, 2010 in U.S. Appl. No. 12/300,675, filed May 3, 2007 by Moller et al.
Non-Final Rejection of Oct. 7, 2008 in U.S. Appl. No. 10/508,104 (US Patent No. 7,678,084; Issue Date Mar. 16, 2010) filed Sep. 15, 2004; First Named Inventor: Jared Alden Judson.
Non-Final Rejection of Mar. 19, 2009 in U.S. Appl. No. 10/508,104 (US Patent No. 7,678,084; Issue Date Mar. 16, 2010) filed Sep. 15, 2004; First Named Inventor: Jared Alden Judson.
English Abstract of EP387854 Published Sep. 19, 1990.
English Abstract of EP422482 Published Apr. 17, 1991.
English Abstract of FR2622457 Published May 5, 1989.
English Abstract of FR2740345 Published Apr. 30, 1997.
Machine Translation of JP09166474 Published Jun. 24, 1997.
English Abtsract of JP4-507059 Published Dec. 10, 1992.
English Abstract of JP 7-500039 Published Mar. 14, 1994.
English Abstract of RU2091087.
English Abstract of RU2212254.
Common Insulin Injection Challenges: HTTP://WWW.BD.COM/US/DIABETES/PAGE.ASPX?CAT=7001&ID=7265.
Owen Mumford Product Range.
Search Report Issued in Connection With European Appln No. 06005602.5, Mailed Oct. 16, 2006.
English Abstract of DE10201875 Published May 22, 2003.
English Abstract of DE102004046003 Published Mar. 30, 2006.
English Abstract of DE19503230 Published Aug. 8, 1996.
English Abstract of DE 19838760 dated Apr. 20, 2000.
English Abstract of DE29513214 Published Feb. 13, 1997.
English Abstract of DE3236374 Published Apr. 5, 1984.
English Abstract of DE3923079 Published Jan. 24, 1991.
English Abstract of DE387854 Published Sep. 19, 1990.
English Abstract of DE422482 Published Apr. 17, 1991.
English Abstract of FR 2622457 Published May 5, 1989.
English Abstract of FR5740345 Published Apr. 30, 1997.
English Abstract of IN165367 Published Mar. 20, 1986.
English Abstract of JP01-100495 Published Apr. 18, 1989.
Machine Translation of JP09166474 Published Jul. 24, 1997.
English Abstract of JP02-126184 Published May 15, 1990.
English Abstract of JP02-182267 Published Jul. 16, 1990.
English Abstract of JP4-224764 Published Aug. 14, 1992.
English Abstract of JP4-507059 Published Dec. 10, 1992.
English Abstract of JP2006250582 Published Sep. 21, 2006.
English Abstract of JP3017167 Published Nov. 30, 1999.
English Abstract of JP56-163486 Published Dec. 16, 1981.
English Abstract of JP7-500039 Published Mar. 14, 1994.
English Abstract of RU 2091087, Published Sep. 27, 1997.
English Abstract of RU2212254, Published Sep. 20, 2003.
Annersten, M. et al., Insulin Pens Dribble From the Tip of the Needle After Injection, Practical Diabetes Int., vol. 17(4), pp. 109-111 (2000).
Beckmann, Sensors, Memory, Circuits, Polyapply Newsletter, vol. 1(3), (2006).
Common Insulin Injection Challenges: http://www.bd.com/us/diabetes/page.aspx?cat=7001&id=7265, Jun. 30, 2010.
Gnanalingham, M.G. et al., Accuracy and Reproducibility of Low Dose Insulin Administration Using Pen-Injectors and Syringes, Downloaded From adc.bmj.com on Jan. 9, 2008.
Search Report Issued in Connection With PCT Appln. No. PCT/EP2007/052630, Mailed Nov. 12, 2007.
Search Report Issued in Connection with European Application No. 06005599.3, Mailed Oct. 4, 2006.
Search Report Issued in Connection With PCT Application No. PCT/EP2007/052633, Mailed Feb. 20, 2008.
Search Report Issued in Connection With European Appln. No. 06005602.5, Mailed Oct. 16, 2006.
Trankler, Hans-Rolf, R. Oldenbourg, Verlag, Munchen, Wien.
Notice of Opposition by Owen Mumford (UK).
Notice of Opposition by Genentech (USA).
Notice of Opposition by Techpharma (CH) Including English Translation.
Opposition in Related European Patent Application EP 02711784.5 of Sep. 19, 2008.
Validity Opinion by the UK PTO.
Abstract of AU2003232576.

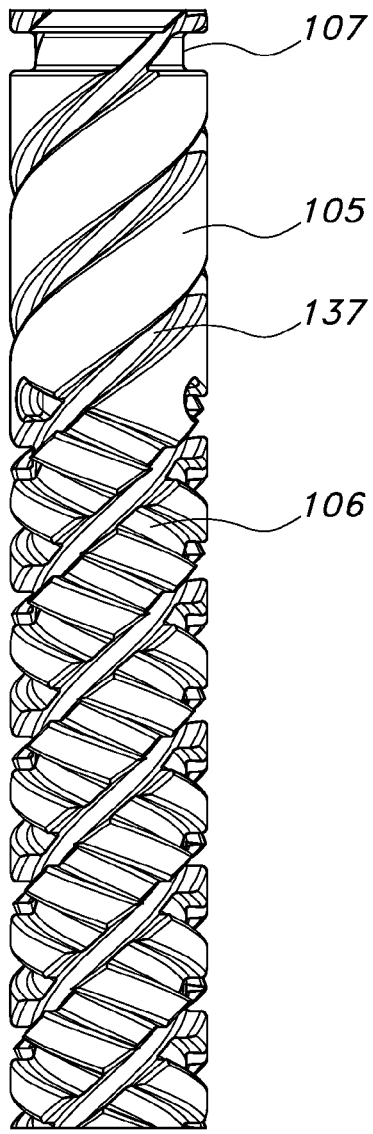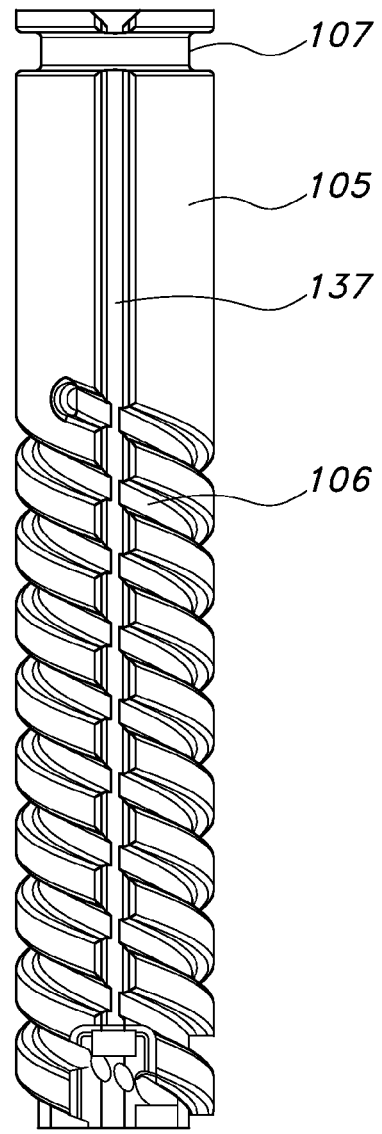
FIG. 6A
FIG. 6B
(PRIOR ART)

INJECTION DEVICE

CROSS-REFERENCE TO RELATED APPLICATIONS

This application is a Continuation of U.S. application Ser. No. 11/911,871 filed Oct. 18, 2007 which is a 35 U.S.C. §371 national stage application of International Patent Application PCT/EP2006/061748 (published as WO 2006/114396), filed Apr. 21, 2006, which claimed priority of Danish Patent Application PA 2005 00589, filed Apr. 24, 2005; this application further claims priority under 35 U.S.C. §119 of U.S. Provisional Application 60/676,713, filed May 2, 2005.

The present invention relates to syringes having a piston drive element for engaging and moving a piston within a medication cartridge, by which a dose can be set by rotating a nut along the piston drive element during dose setting, and wherein a set dose can be expelled by driving the nut to its initial position.

BACKGROUND OF THE INVENTION

An almost classic pen which adopts the above described dose setting and injecting scheme is described in EP 327 910.

By setting a dose on this pen a tubular member forming an injection button is screwed up along a threaded piston rod a distance corresponding to the distance said piston rod must be moved to inject the set dose. The tubular member simply forms a nut which is during the dose setting screwed away form a stop and which is during the injection pressed back to abutment with said stop and the force exerted on the button is directly transmitted to the a piston closing one end of an ampoule in the syringe which ampoule contains the medicament to be injected. When the piston is pressed into the ampoule the medicament is pressed out through a needle mounted through a closure at the other end of the ampoule.

By time it has been wanted to store larger amount in the ampoules, typically 3 ml instead of 1.5 ml. As it has not been appropriate to make the syringe longer the ampoule is instead given a larger diameter, i.e. the area of the piston facing the medicament in the ampoule has been doubled and consequently the force which has to be exerted on the piston to provide the same pressure as previously inside the ampoule has been doubled. Further the distance the piston has to be moved to inject one unit of the medicament has been halved.

This development is not quite favourable, as especially users having reduced finger strength have their difficulties in pressing the injection button, a problem that is further increased when still thinner needles are used to reduce the pain by injection. Also with quite small movements of the button it is difficult to feel whether the button is moved at all and by injection of one unit from a 3 ml ampoule the piston and consequently the injection button has to be moved only about 0.1 mm.

Consequently a wish for a gearing between the injection button and the piston has occurred so that the button has a larger stroke than has the piston. By such a gearing the movement of the injection button is made larger and the force, which has to be exerted on the injection button, is correspondingly reduced.

In EP 608 343 a gearing is obtained by the fact that a dose setting element is screwed up along a spindle having a thread with a high pitch. When said dose setting element is pressed back in its axial direction the thread will induce a rotation of said dose setting element, which rotation is via a coupling transmitted to a driver nut with a fine pitch which driver nut will force a threaded not rotatable piston rod forward.

A similar gearing is provided in WO 99/38554 wherein the thread with the high pitch is cut in the outer surface of a dose setting member and is engaged by a mating thread on the inner side of the cylindrical housing. However, by this kind of gearing relative large surfaces are sliding over each other so that most of the transformed force is lost due to friction between the sliding surfaces. Therefore a traditional gearing using mutual engaging gear wheels and racks is preferred.

From WO 96/26754 is known an injection device wherein two integrated gear wheels engages a rack fixed in the housing and a rack inside a plunger, respectively. When the plunger is moved axially in the housing the rack inside this plunger can drive the first gear wheel to make the other integral gear wheel move along the fixed rack in the housing. Thereby the gear wheel is moved in the direction of the plunger movement but a shorter distance than is this plunger and this axial movement of the integrated gear wheels is via a housing encompassing said gear wheels transmitted to a piston rod which presses the piston of an ampoule further into this ampoule. However, the rack inside the plunger is one of a number axial racks provided inside said plunger. These racks alternates with untoothed recesses, which allow axial movement of the plunger without the first gear wheel being in engagement with a rack in this plunger. This arrangement is provided to allow the plunger to be moved in a direction out of the housing when a dose is set. When the plunger is rotated to set a dose it is moved outward a distance corresponding to one unit during the part of the rotation where the first gear wheel passes the untoothed recess, thereafter the first gear wheel engages one of the racks so the set unit can be injected, or the rotation can be continued to make the first gear wheel pass the next recess during which passing the set dose is increased by one more unit and so on until a dose with the wanted number of units is set.

A disadvantage by this construction is that the teeth of the racks and gearwheels alternating have to be brought in and out of engagement with each other with the inherit danger of clashing. As only a few racks separated by intermediary untoothed recess can be placed along the inner surface of the plunger only few increments can be made during a 360° rotation.

In U.S. Pat. No. 6,663,602 is disclosed an injection device, wherein a direct gearing, i.e. a gearing by which more transformations of rotational movement to linear movement and linear movement to rotational movement are avoided, between the injection button and the piston rod.

The injection device shown in U.S. Pat. No. 6,663,602 comprises a housing wherein a piston rod threaded with a first pitch is non rotatable but longitudinally displaceable guided, a nut engaging the thread of the piston rod which nut can be screwed along the threaded piston rod away from a defined position in the housing to set a dose and can be pressed back to said defined position carrying the piston rod with it when the set dose is injected, a dose setting member which can be screwed outward in the housing along a thread with a second pitch to lift an injection button with it up from the proximal end of the housing. This injection device is provided with a gearbox which provides a gearing between the axial movements of the injection button and the nut relative to the housing which gearing has a gearing ratio corresponding to the ratio of said second and first pitch.

Although broadly being considered state of the art, the injection device disclosed in U.S. Pat. No. 6,663,602 presents important mechanical constraints due to the construction principle of the linear gearing system which acts during dosing. According to the injection device of U.S. Pat. No. 6,663,602, the length of the nut/piston rod assembly is increased during the dose setting by rotating the nut in a thread on the piston rod. During dosing, the linear displacement of the nut and the injection button are coupled such that there is proportionality between the movement of the nut and the injection button, the proportionality given by the transmission ratio of the gear box. As the nut is rotationally confined relatively to the piston rod during dosing, the translation of the nut corresponds to the translation of the piston rod and thus ultimately to the dose of medication administered.

As the gear is an integrated part of the construction and as the gear can only be designed to certain transmission ratios, the gear implies important constraints on the obtainable ratio of movement of the injection button relative to the movement of the piston. Due to the direct proportionality between the movement of the piston rod and the administered dose of medication, the same syringe can not easily be adapted to different medications. Although adaptation is possible by changing the transmission ratio of the linear gear, this solution will in general be very complex and imply a complete redesign of the syringe.

DISCLOSURE OF THE INVENTION

The injection devices disclosed in U.S. Pat. No. 6,663,602 comprises dose setting and injection mechanisms wherein the nut is held rotationally fixed during dose delivery. However, according to the present invention, the nut may be rotated relative to the housing, also during dose delivery.

According to one aspect of the present invention, the injection device comprises:
a. a housing for a dose setting and injecting mechanism, the housing having a proximal end and a distal end,
b. a rotatable dose setting member,
c. an axially displaceable piston rod having a first thread and an additional longitudinally extending track,
d. a central opening in the housing for engaging the additional longitudinally extending track of the piston rod, thus guiding the angular movement of the piston rod during axial translation of the piston rod,
e. a threaded nut engaging the first thread of the piston rod, the nut being rotatably locked to the dose setting member during dose setting,
f. a rotational coupling mechanism having a coupling member which is axially displaceable from a first position to a second position, the rotational coupling mechanism allowing rotational movement of the nut relative to the coupling member during dose setting while preventing rotational movement during injection. The coupling member is rotationally coupled to the housing so as to be urged to rotate as a function of axial displacement of the coupling member relative to the housing during at least a part of the axial displacement from said first to said second position.

According to such a configuration, a prolongation or reduction of the stroke of the injection button compared to the stroke of the piston rod may be obtained. Further, as this configuration implies a change in the rate of rotation of the dose setting member for a given dose to be injected, a dose scale reading with a different layout may be obtained. In this way, a scale reading with increased distance between consecutive numbers may be obtained, which provides the possibility of increasing the font size of the labels of the scale reading. Also, this configuration provides the possibility of fine tuning the gearing ratio, if the injection device is so configured.

According to a second aspect of the invention, the dose setting member is axially displaceable as a result of rotation of the dose setting member relative to the housing, while the coupling member is coupled to the dose setting member such that axial displacement of the dose setting member substantially corresponds to axial displacement of the coupling member.

According to a third aspect of the invention, the coupling member has a thread and is threadedly engaged with a helical thread disposed in the housing, the thread of the housing having a constant pitch. According to this aspect, a particularly simple solution is obtained.

According to a fourth aspect of the invention, the coupling member has a thread which engage a longitudinally extending track disposed in the housing wherein the longitudinally extending track has a variable pitch along the extension of the track. According to this aspect, the rotation of the dose setting member is nonlinear with respect to the various specific dose selections. Thus, a dose setting member with a nonlinear scale is obtainable, e.g. a scale can be provided having comparable larger steps for smaller doses to be injected than for larger doses. This implies improved resolution in the low range of injectable doses. Also, an injection button can be provided having a stroke that is nonlinear with respect to the specific amount of drug to be injected, e.g. having a prolonged stroke for smaller doses compared to the solutions provided for in U.S. Pat. No. 6,663,602.

According to a fifth aspect of the invention, the rotational coupling mechanism comprises an incremental feedback mechanism providing incremental clicks during dose setting corresponding to dose volume. This aspect provides an easy adjustment of the rotational movement of the dose setting drum for each click, relatively to the housing part. In combination with the third aspect, an increase or a decrease of distance between the numbers on the dose setting drum or dose setting scale and thus the rotation for each click can be varied by choosing a specific pitch of the thread of the housing which engages the thread of the coupling member. By varying the inclination of the track along the extension of the track, it is possible to vary the rotation per click in a nonlinear way.

According to a sixth aspect of the invention, an injection button is operatively connected to a gear box assembly coupling axial movement of the injection button with axial movement of the nut. A gearing between the movements of the injection button and the nut may be obtained by the gearbox comprising at least one gear wheel carried by a connector which projects from the gear box longitudinally displaceable but non rotatable relative to said gearbox and is integral with the nut, a first rack integral with a first element of the gearbox, which element is rotational but not longitudinally displaceable relative to the housing, and second element carrying a second rack projecting from said gearbox longitudinally displaceable but non rotatable relative to said first element and being coupled to the injection button to follow longitudinal movements of said button, the at least one gear wheel engaging the first and the second rack, respectively, and being dimensioned to provide a gearing by which a longitudinal movement of the second rack is transformed to a longitudinal movement of the connector with a gearing ratio for the mentioned longitudinal movements of the second rack and the connector relative to the housing, which gearing ratio substantially corresponds to the ratio of said second to said first pitch.

In such a device only the forces necessary to drive the dose setting member are transformed by a thread with a high pitch whereas the forces necessary to move the piston by injection is transmitted to said piston through a conventional gear with constantly engaging gears and racks.

In a seventh aspect of the invention, the piston rod is provided with a stop for the movement of the nut along the thread of said piston rod, thereby forming an end-of-content stop. This way a dose setting limiter is provided in the classic way, which involves no additional members to prevent setting of a dose exceeding the amount of liquid left in the ampoule.

According to an eighth aspect of the invention, the additional longitudinally extending track on the piston rod is helically disposed on the external surface of the piston rod thereby forming a second thread on the piston rod. By forming this track in a helical fashion, the piston rod is rotated as a result of axial displacement of the piston rod relative to the housing. By rotating the piston rod and the coupling member a similar angle during dosing, it is possible to set smaller or bigger dose volume per click, and still have an EOC (End-Of-Content) stop between the piston rod and the nut.

As used herein, the term "drug delivery device" according to the instant invention shall mean a single-dose or multi-dose, disposable or re-useable device designed to dispense a selected dose of a medicinal product, preferably multiple selected doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, preferred embodiment the term drug delivery device shall mean a disposable multi-dose pen-type device having mechanical and manual dose delivery and dose selection mechanisms, which is designed for regular use by persons without formal medical training such as patients. Preferably, the drug delivery device is of the injector-type.

The term "housing" according to instant invention shall preferably mean an exterior housing ("main housing", "body", "shell") or interior housing ("inner body", "insert") having internal and external threads. The housing may be designed to enable the safe, correct, and comfortable handling of the drug delivery device or any of its mechanisms. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed. However, a cartridge may be directly coupled to the housing so as to be partly or fully external to the housing.

The term "engaged" according to instant invention shall particularly mean the interlocking of two or more components of the drive mechanism/drug delivery device, e.g. a spline or thread connection, preferably the interlocking of helical threads of components ("threadedly engaged"). The term "engaged" encompasses the use of intermediary components coupling threadedly engaged threads.

The term "thread" according to instant invention shall preferably mean a full or part thread, e.g., a cylindrical spiral rib/groove, usually of helical nature or comprising linear inclined parts, located on the internal and/or external surface of a component of the drug delivery device ("internal thread" and/or "external thread"), having an essentially triangular or square or rounded section designed to allow continuous free rotational and/or axial movement between components. Optionally, a thread may be further designed to prevent rotational or axial movement of certain components in one direction.

The term "dose setting member" according to instant invention shall mean an essentially tubular component of essentially circular cross-section having either: a) both an internal and external thread, or b) an internal thread, or c) an external thread. The dose setting member may be designed to indicate a selected dose of a dispensable product. This may be achieved by use of markings, symbols, numerals, etc., e.g. printed on the external surface of the dose setting member or an odometer, or the like. Also, a separate dose scale may be used, either comprising a mechanical or an electronic display.

The term "lead" according to instant invention shall preferably mean the axial distance a nut would advance in one complete revolution; preferably "lead" shall mean the axial distance through which a component having a helical thread, i.e. dose setting member, nut, piston rod, etc., of the drive mechanism travels during one rotation. Therefore lead is a function of the pitch of the thread of the relevant component.

The term "pitch" according to instant invention shall preferably mean the distance between consecutive contours on a helical thread, measured parallel to the axis of the helical thread.

The term "piston rod" according to instant invention shall mean a component adapted to operate through/within the housing, designed to translate axial movement through/within the drug delivery device, preferably from the nut to the piston, for the purpose of discharging/dispensing an injectable product. Said piston rod may be flexible or not. It may be a simple rod, a lead-screw, or the like. The "piston rod" according to instant invention shall further mean a component having a non-circular cross-section and preferably having one or more threads located partly or fully extending along its length. It may be made of any suitable material known by a person skilled in the art.

The term "incremental feedback mechanism" according to instant invention shall mean a mechanism providing the dose setting to occur in a number of discrete incremental steps, e.g. one incremental click for each international unit being set, the incremental feedback mechanism preferably providing a tactile or audible click which can be sensed or heard by a user operating the pen.

BRIEF DESCRIPTION OF THE DRAWINGS

In the following the invention is described in further details with references to the drawing, wherein FIG. 1 schematically shows a sectional view of an injection device according to the invention, FIG. 6a shows a large scale view of the tubular part 105 of FIG. 5 according to one embodiment of the invention, and FIG. 6b shows a large scale view of the corresponding part 105 of a prior art injection device.

DESCRIPTION OF EXEMPLARY EMBODIMENTS

The device shown in the appended drawings is shown as an injector pen, which pen has an elongated body with a central axis. However, other forms are within the scope of the invention.

Figure 1:
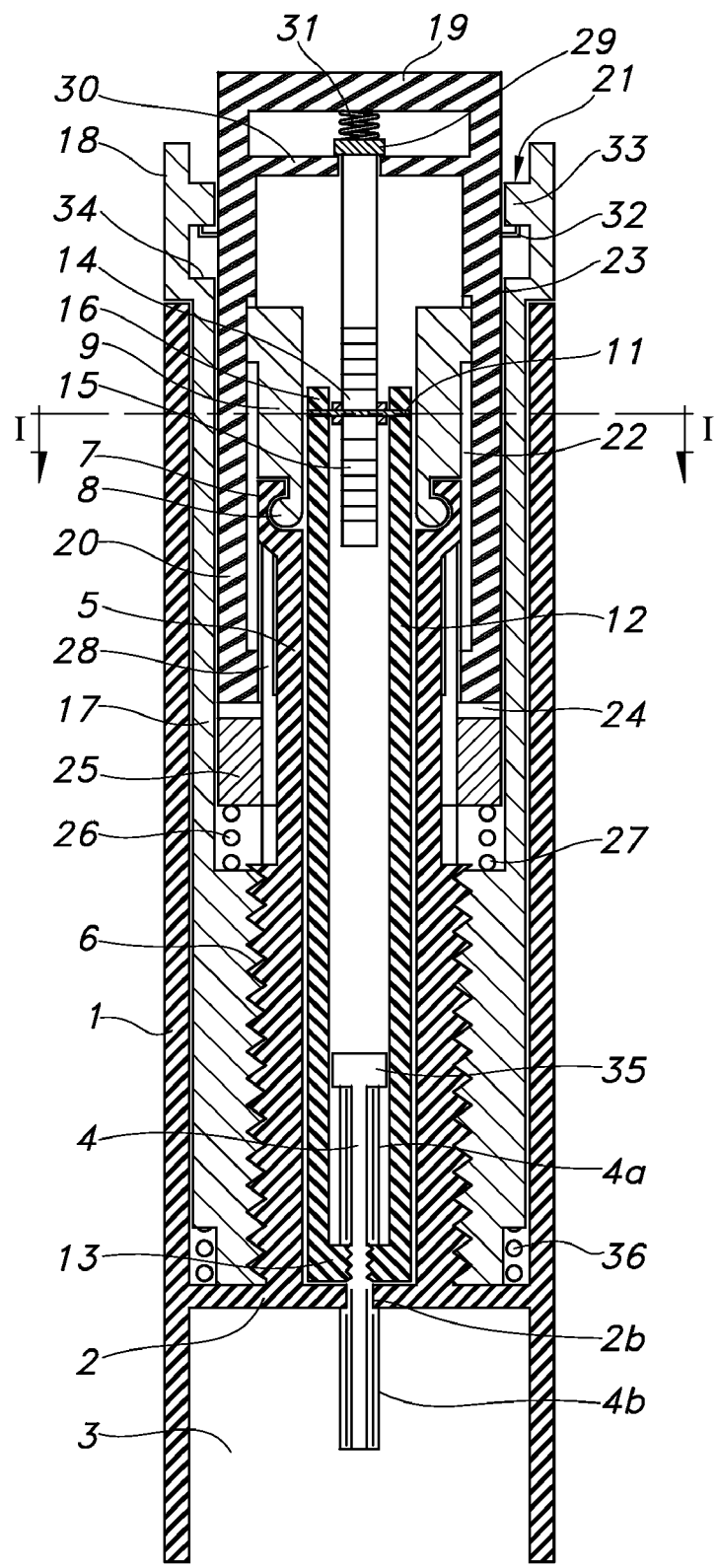

In the device shown in FIG. 1 an elongated cylindrical housing 1 has a partitioning wall 2 which divides the housing in a compartment containing a dose setting mechanism and a compartment 3 designed for the accommodation of a not shown ampoule. The partitioning wall 2 is provided with an opening extending there through. Alternatively, the wall may be replaced by an insert which is secured against rotational and axial motion with respect to the main structure of the housing 1, the opening being formed in said insert. A piston rod 4 having a first thread 4a and an additional longitudinally extending track 4b formed in or on the piston rod 4, extends through the opening 2b, which is provided with one or more ribs which mates and engages the additional longitudinal extending track 4b.

In accordance with the specific design of the additional longitudinally extending track 4b and the mating opening 2b in partition wall 2, the piston rod 4 is rotationally guided as a function of axial displacement of the piston rod. To obtain a piston rod 4 which is longitudinally displaceable while being rotationally locked relative to the housing, the additional longitudinally extending track 4b is formed as a rectilinear track which extends parallel to the axis of the piston rod 4. Alternatively, to obtain a piston rod 4 which is being rotated as a function of axial displacement of the piston rod 4, the additional longitudinal track 4b is formed as a helical groove or thread which mates and engages with helical ribs or threads formed in opening 2b in the partition wall 2.

In accordance with the specific design of the injection device, the first thread 4a and the additional longitudinally extending track 4b may be disposed on opposite ends of the piston rod 4, may be partly overlapping or fully overlapping in the axial direction of the piston rod 4. Furthermore, the thread 4a may be disposed with a larger depth than the additional longitudinally extending track 4b or vice versa. In FIG. 1, the threads 4a and 4b and the threaded opening 2b are schematically represented.

Concentrically with the housing 1 the wall 2 carries on its side turning away from the compartment 3 a tubular element 5 which is at a part of it adjacent to the wall 2 provided with an outer thread 6 and which has at its free end a circumferential recess 7. A ring shaped coupling element 8 on a gear box 9 engages the recess 7. By this coupling the gearbox is fixed in the housing 1 in a way that allows the gearbox 9 to rotate in the housing but not to be axially displaced relative to said housing.

In the gearbox 9 a gear wheel assembly comprising two integral gear wheels is journaled on a shaft 11, which runs perpendicular to the longitudinal axis of the device between two axial connection bars 12. The connection bars 12 project from the gear box towards the partition wall 2 and are connected to a nut 13 which engages the first thread 4a of the piston rod 4. The gear wheel assembly comprises a gear wheel 14 with a large diameter engaging the teeth of a rack 15 which is guided in the gear box to be displaced in the longitudinal direction of the device, and a gear wheel 16 with a small diameter engaging a rack 10 in FIG. 2 extending in the longitudinal direction of the device on the inner wall of the gearbox 9. The gear wheel 16 with the small diameter may be divided into two gear wheels placed on each side of the of the gear wheel 14, and the rack on the inner wall of the gearbox 9 may have a longitudinal recess without any teeth to make room for the gear wheel 14.

A tubular dose setting member 17 fitting into the housing 2 is at an end provided with an internal thread mating and engaging the outer thread 6 of the tubular element 5 and has at its other end a part with enlarged diameter forming a dose setting button 18. Due to the engagement with the thread 6 the dose setting member 17 may be screwed in and out of the housing to show a number on a not shown helical scale on its outer surface in a not shown window in the housing 1.

A bottom 19 in a deep cup shaped element, which has a tubular part 20 fitting into the dose setting member 17 and encompassing the gearbox 9, forms an injection button. Coupling means between the dose setting member 17 and the cup shaped element ensures that rotation of the dose setting member 17 is transmitted to the cup shaped element. Further the inner wall of the tubular part 20 has longitudinal recesses 22 engaged by protrusions 23 on the gearbox 9 so that rotation of the dose setting member 17 via the cup shaped element is transmitted to the gearbox 9.

At the edge of the open end of the cup shaped element a rosette of V-shaped teeth are provided, which teeth engage a corresponding rosette of V-shaped teeth 24 on a coupling member 25 which is pressed against the edge of the cup shaped element by a spring 26 which is compressed between a not toothed side of the coupling member 25 and a round going shoulder 27 on the inner wall of the dose setting member 17 at an inner end of the inner thread of this member. The coupling member 25 is provided with one or more inner protrusions forming a thread 28, which is engaged by a thread or track 37 on the tubular element 5 so that the coupling member 25 will be forced to rotate when it is displaced axially relative to the housing. The track 37 may be designed as a helical thread with a constant pitch along the extension of the track. Alternatively, the layout of the pitch may be formed with a variable pitch along the extension of the track, e.g. by forming a track with inclined as well non-inclined rectilinear steps, or curved parts.

The track 37 is so shaped that the dose setting member 17 rotates relative to the coupling member 25, when a user dials a dose by rotating the dose setting button 18. In this way a click coupling is established which makes a click noise when the V-shaped teeth at the edge of the cup shaped element by rotation of this element rides over the V-shaped teeth of the coupling member 25, i.e. an incremental feedback mechanism is provided.

A head 29 on the projecting end of the rack 15 is with a play fixed at the bottom of the cup shaped element between the bottom 19 forming the injection button and an inner wall 30 near this bottom. The rack is fixed in a position with its head pressed against the wall 30 by a spring 31 between the bottom 19 and the head 29.

To set a dose the dose setting button 18 is rotated to advance the dose-setting member 17 in the proximal direction in accordance with the thread 6. Due to the coupling 21 the cup shaped element will follow the rotation of the dose-setting member 17 and will be lifted concurrently with this member up from the end of the housing 1. During dose setting, the respective amount of axial displacement of the dose setting member 17 and the injection button 19 depends on the pitch of the thread 6, the pitch of the first thread on the piston rod 4 and the gear ratio. Also, if the piston rod 4 is allowed to move during dose setting, the axial and rotational movement of the piston rod 4 influences the amount that the injection button will be displaced. By the rotation of the cup shaped element the V-shaped teeth 24 at the edge of its open end will ride over the V-shaped teeth of the coupling member 25 to make a click sound for each unit the dose is changed. A too high set dose can be reduced by rotating the dose setting button 18 in the opposite direction of the direction for increasing the dose. When the dose setting member is screwed along the thread 6 on the tubular element 5, the coupling member 25 will follow the dose setting member in its axial movement as the spring 26 is supported on the shoulder 27.

The spring will keep the V-shaped teeth of the coupling member 25 and the cup shaped element in engagement and maintain in engagement the coupling 21, which may comprise Δ-shaped protrusions 32 on the cup shaped element engaging Λ-shaped recesses in an inner ring 33 in the dose setting button 18.

Due to the axial displacement of the dose setting member 17 during dose setting, the coupling member 25 is axially displaced as well. According to the specific design of the threads or tracks 28 and 37, the coupling member 25 is forced to rotate as the coupling member 25 is axially displaced. In some embodiments, the thread 37 is formed as a helical thread which has a constant pitch along the length of the total axial distance that the coupling member is allowed to move. Depending on the direction of rotation of track 37, the dose setting button 18 has to be rotated a larger or smaller angle for each click to occur compared to a situation where the coupling member is kept rotationally fixed. A corresponding amendment of the layout of the scale reading may be provided, e.g. by forming the dose scale with larger or smaller spaces between neighboring dose values.

The rotation of the dose setting button 18 and the cup shaped element is further transmitted to the gearbox 9 through the protrusions 23 on this gearbox engaging the longitudinal recesses 22 in the inner wall of the tubular part 20 of said cup shaped element. The rotation of the gearbox 9 is through the connection bars 12 transmitted to the nut 13, which in this way is advanced along the first thread 4a of the piston rod 4 and lifted away from its abutment with the wall 2 when a dose it set. As the dose is set by moving the nut 13 on the piston rod which operates the piston in the not shown ampoule in the compartment 3, a dose setting limiter, which ensures that the size of the set dose does not exceed the amount of medicament left in the ampoule, can easily be established by providing the piston rod 4 with a stop 35 which limits the movement of the nut 13 up along the piston rod 4.

Due to the confinement of the head 29 in the space between the bottom 19 and the wall 30 of the cup shaped element, the rack 15 is drawn with the injection button outward. Depending on the specific gear ratio of the gear assembly, the outward movement of the rack 15 corresponds to an outward movement of nut 13. As the nut 13 is rotated during dose setting, the length of the piston rod/nut assembly is prolonged, depending on the mutual pitch of the piston rod/nut threads and depending on the actual design of the additional longitudinally extending track 4b.

By varying the pitch of the different threads or the gear ratio, the piston rod is either moved distally, proximally or held stationary during dose setting.

Figure 2:
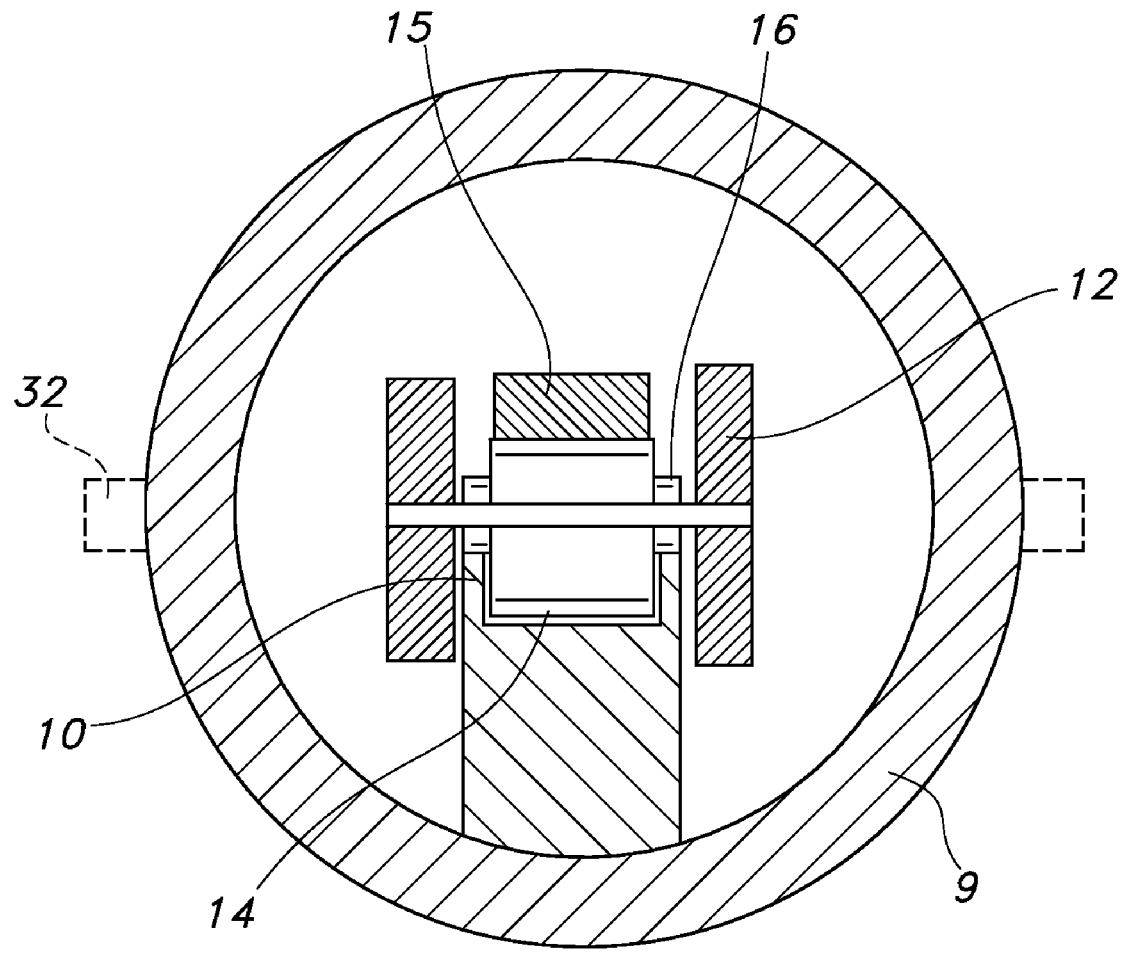
FIG. 2 shows schematically a sectional view of the gear box along the line I-I in FIG. 1.

Ideally, if no axial movement of the piston rod 4 is wanted during dose setting the pitch of the thread 6 and the thread formed in the piston rod 4a as well as the pitch of the outer recess (6) should be matched exactly to the gearing ratio of the gear box depicted in FIG. 2.

However, tolerances in the machining of the components comprising the pen may lead to a slight unintended mismatch of the pitches relatively to the transmission ratio of the gearbox 9. Especially the situation where the piston rod 4 advances slightly during dose setting is highly undesirable as the injection device during dose setting will expel a small amount of medication.

This situation is avoided by mismatching one or more of the above mentioned pitches to the transmission ratio of the gearbox such that the piston rod 4 is slightly withdrawn during dose setting. The mismatch of pitches is most simply implemented by modification of the pitch of the recess 4a made in the piston rod 4 and the corresponding thread in the nut 13. In addition, if the additional longitudinally extending track 4b on piston rod forms a helical thread, i.e. allowing the piston rod 4 to rotate with respect to the housing (1), this threaded connection has to be taken into account when designing the mechanism.

Alternatively, the injection device is designed such that the recess in the piston rod is initially designed to be axially aligned with the piston rod. On assembled production prototypes the advance of the piston rod during dose setting is measured. Hereafter the axial aligned recess is redesigned to a helical recess where the superimposed rotation of the piston rod during dose setting compensates for the tolerances in the machining.

According to one embodiment of the invention the pitches of the threaded parts and the linear gearing are matched such that the piston rod retracts between 0% and 2% of the full linear translation relatively to the cartridge during dose setting.

A corresponding solution can be provided in the injection device shown in U.S. Pat. No. 6,663,602 which contains an injection device having a coupling member 25, which is kept rotationally locked with respect to the housing. For that particular injection device, a slight mismatch of either the thread 6 or the thread of piston rod 4 to the transmission ratio of the gearbox can be provided such that the piston rod 4 is slightly withdrawn during dose setting.

In the device according to the instant invention, to inject a set dose the injection button is pressed by pressing on the bottom 19. In the initial phase of the pressing, the spring 31 is compressed where after the pressing force is directly transmitted to the head 29 of the rack 15 and this way to the rack 15 itself. Through the gear box 9 the force is transformed and is transmitted through the connection bars 12 to the nut 13 which will press the piston rod 4 into the compartment 3 until the dose-setting member 17 abuts the wall 2.

During the initial phase of the movement of the injection button the Δ-shaped protrusions 32 on the cup shaped element will be drawn out of their engagement with the Λ-shaped recesses in the ring 33. The dose-setting member 17 can now rotate relative to the injection button and will do so when the Δ-shaped protrusions 32 press against a shoulder 34 at the bottom of the dose setting button 18. Only a force sufficient to make the dose setting member rotate to screw itself downward along the thread 6 is necessary as the force necessary to make the injection is transmitted to the piston rod 4 through the gearbox 9. A helical reset spring 36 concentric with the dose setting member can be mounted at the lower end of this member and can have one end anchored in the dose setting member 17 and the other end anchored in the wall 2. During setting of a dose this spring may be tighter coiled so that on the dose setting member it exerts a torque approximately corresponding to the torque necessary to overcome the friction in the movement of the dose setting member along the thread 6 so that the force which the user have to exert on the injection button is only the force necessary to drive the piston rod into an ampoule to inject the set dose.

It shall be noticed that use of only one size gear wheel which engages as well the rack 15, which is movable relative to the gear box 9, as the rack 10, which is unmovable relative to the gear box, provides a gearing ratio of 2:1 for the longitudinal movement relative to the syringe housing 1 for the movable rack 15 and the connector 12, which carries the shaft 11 of the gear wheel.

Figure 3:
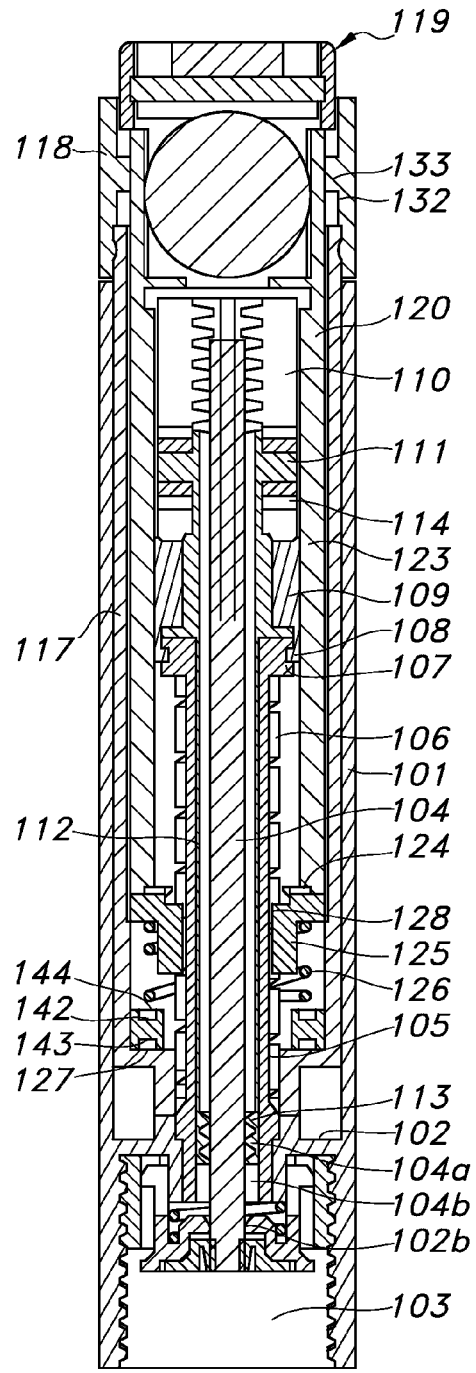
FIG. 3 shows a longitudinal sectional view in the dose setting part of another embodiment of an injection device according to the invention.
Figure 4:
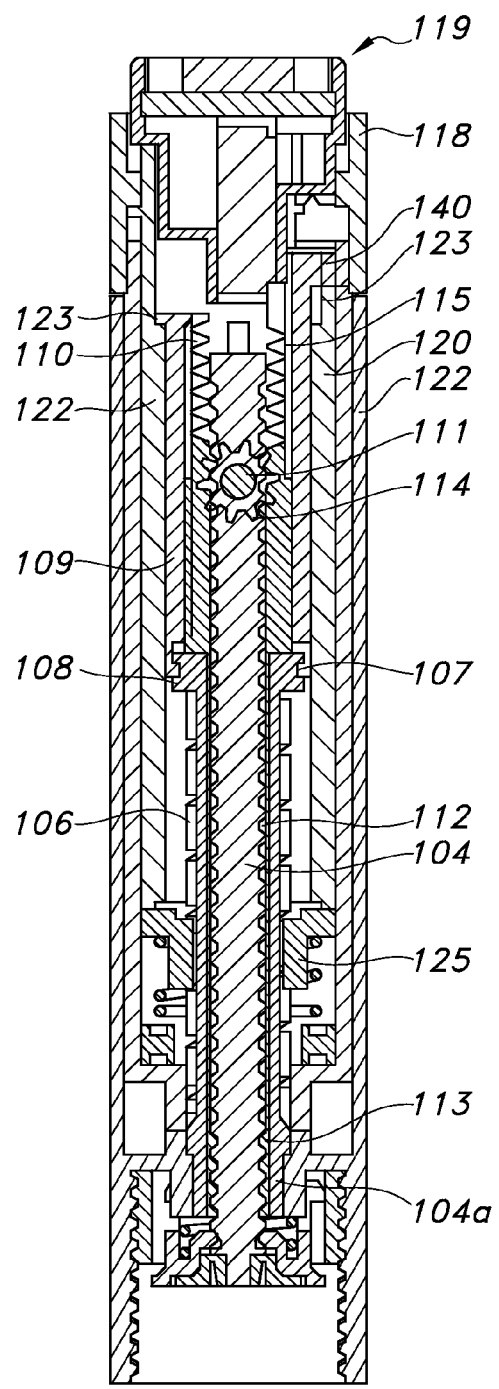
FIG. 4 shows a longitudinal sectional view perpendicular to the view in FIG. 3.

FIGS. 3 and 4 shows an embodiment wherein only one size gear wheel is used and wherein elements corresponding to elements in FIGS. 1 and 2 are given the same references as these elements with a prefixed "1".

For manufacturing reasons minor changes are made. So the partitioning wall 102 and the tubular element 105 are made as two parts which are by the assembling of the device connected to each other to make the assembled parts act as one integral part. The same way the dose setting member 117 and the dose setting button 118 are made as two parts, which are fixed firmly together.

A circumferential recess 107 is provided as an outer recess at the free end of the tubular part 105 and a ring shaped coupling element is provided as an inner bead 108 on the gearbox element 109 which bead engages the recess 107 to provide a rotatable but not axially displaceable connection between the tubular part 105 and the gearbox.

A tubular element 120 having ridges 122 which engages recesses 123 on the gearbox and is at its upper end closed by a button 119 from which a force provided by pressing this button is transmitted to the tubular element 120.

The gearbox is formed by two shells, which together form a cylinder fitting into the tubular element where the shells are guided by the engagement between the ridges 122 and the recesses 123. Racks 110 and 115 are provided along edges of the shells facing each other. One shell forming the gearbox part 109 is provided with the inner bead 108, which engages the circumferential recess 107 at the end of the central tubular part 105 and carries the rack 110. The other shell is axially displaceable in the tubular element 120 and forms the rack 115. At its outer end projecting from the gearbox the shell carrying the rack 115 is provided with a flange 140 which is positioned in a cut out 141 in the end of the tubular element 120 carrying the button 119 so that this button and the tubular element 120 can be moved so far inward in the device that the engagement of the teeth 132 and 133 can be released before the button 119 abuts the flange 140.

A tubular connection element 112 connects the threaded piston rod 104 with the gearbox. At its end engaging the piston rod 104 the connection element has a nut 113 with an internal thread mating the external thread 104a of the piston rod 104. At its end engaging the gear box the connection element is provided with two pins 111 projecting perpendicular to the longitudinal axis of the connection element 112 at each side of this element. Each pin 111 carries a gear wheel 114 which is placed between and engages the two racks 110 and 115. This way the connection element 112 will be rotated with the gear box but can be displaced axially relative to said gear box when the racks 110 and 115 are moved relative to each other. In practice it will be the rack 115, which is moved relative to the gearbox element 109 and the housing 1 and will by the shown construction result in a movement of the connection element 112 relative to housing a distance which is half the distance which the rack 115 is moved. A coupling member 125 which is at its periphery provided with a rosette of teeth 124 and has a central bore fitting over the central tube in the housing 101 so that this coupling member 125 can be axially displaced along said central tube 105. One or more internal protrusions 128 on the central bore of the coupling member 125 is shown in FIGS. 3 and 4. The protrusions engage mating helical recessed tracks or threads 137 (not shown in FIGS. 3 and 4) in the central tube to make the coupling member 125 confined with respect to rotational movements, that is, the coupling member 125 being angularly moved in accordance with the axial displacement of the coupling member 125 along the tracks or threads 137. Due to this rotational confinement or rotational guiding in the housing, a rosette of teeth at the edge of the tubular element 120 can click over the teeth 124 of the coupling member when said tubular element is rotated together with the dose setting member 117. A spring 126 working between the coupling member 125 and an internal shoulder 127 provided in the dose setting member 117 makes the coupling member follow the tubular element 120 when this element with the dose setting member is moved longitudinally in the housing. To make the dose setting member easy rotatable, especially when said dose setting member is pressed inward in the housing, a roller bearing having an outer ring 142 supported by the shoulder 127 and an inner ring 143 supporting a pressure bushing 144 which supports the spring 126. By the provision of this smooth running support only very small axial forces are needed to rotate the dose setting member 117 back to its zero position when a set dose is injected. This solution replaces the provision of a reset spring as the spring 36 in FIG. 1. The bearing is shown as a radial bearing but can be replaced by an axial bearing.

Figure 5:
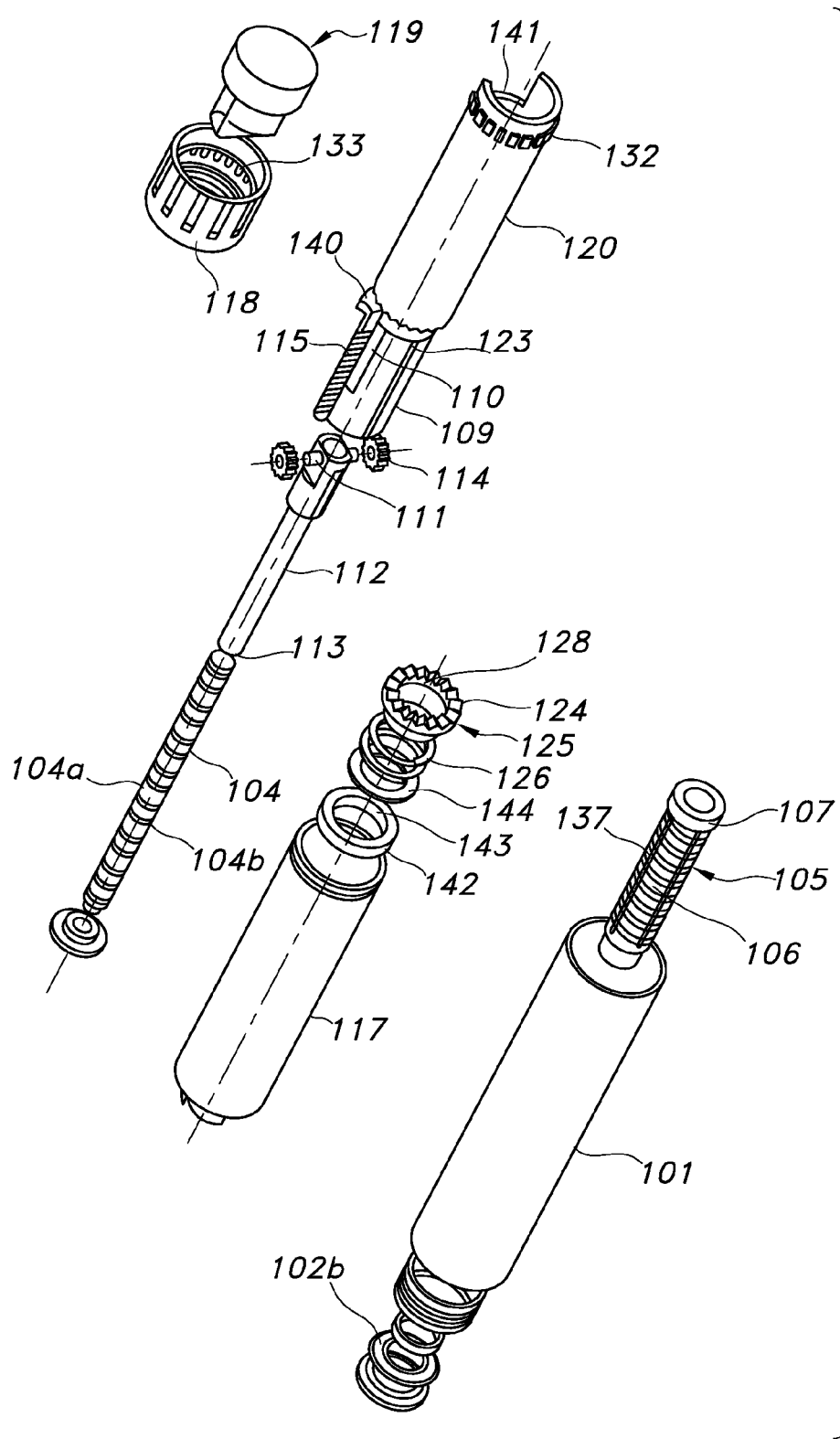
FIG. 5 shows an exploded view of the of the device shown in FIGS. 3 and 4.

Whereas the track 137 is not shown in FIGS. 3 and 4, this track can be viewed in FIG. 5 which depicts an exploded view of the embodiment shown in FIGS. 3 and 4. The central tubular part 105 is further shown in a greater scale in FIG. 6a while FIG. 6b the corresponding part of prior art injection shown in U.S. Pat. No. 6,663,602.

Table 1 is a list showing different configurations of the above-described injection device. In table 1, configuration no. 1 corresponds to the device which is disclosed in U.S. Pat. No. 6,663,602, i.e. a device having a piston rod that is non-rotational but axially displaceable and having a track 37, 137 which is a rectilinear track which extends parallel to the axis of the injection device.

Configurations no. 2-6 correspond to embodiments having the same pitch of the threads 6, 106 on the dose setting member and the first thread 4a, 104a on the piston rod as in configuration no. 1. In configuration no. 2-6, the track 37, 137 is formed as a helical track having a constant pitch along the extension of the track, each of the configurations corresponding to specific pitches of the track. Configurations 1-4 have a piston rod that is non-rotational but axially displaceable. Configurations no. 5 and 6 has a helical track 4b, 104b which mates and engages the threaded opening 2b in the housing.

TABLE 1

| Configuration | Pitch of dose setting member relative to housing First pitch (6, 106) on the tubular part | Pitch (28, 128) on coupling member relative to housing Second pitch on the tubular part (37, 137) | Pitch of piston rod relative to nut (13, 113) First pitch (4a, 104a) on the piston rod | Pitch of piston rod relative to housing Second pitch (4b, 104b) on the piston rod |
|---|---|---|---|---|
| 1 | 7.2 | 0 | 3.6 | 0 |
| 2 | 7.2 | −14.4 | 3.6 | 0 |

TABLE 1-continued

| Configuration | Pitch of dose setting member relative to housing First pitch (6, 106) on the tubular part | Pitch (28, 128) on coupling member relative to housing Second pitch on the tubular part (37, 137) | Pitch of piston rod relative to nut (13, 113) First pitch (4a, 104a) on the piston rod | Pitch of piston rod relative to housing Second pitch (4b, 104b) on the piston rod |
|---|---|---|---|---|
| 3 | 7.2 | −7.2 | 3.6 | 0 |
| 4 | 7.2 | 14.4 | 3.6 | 0 |
| 5 | 7.2 | −7.2 | 3.6 | −3.6 |
| 6 | 7.2 | −14.4 | 3.6 | −7.2 |

(Positive pitch values indicates left handed threads, negative pitch values indicates right handed threads, 0 (Zero) indicates a non rotational longitudinally track).

TABLE 2

| Example # | Configuration | Input Rotation of the dose setting member (17, 117) (in degrees) | Output Relative rotation between the dose setting member and the coupling member (25, 125) (in degrees) | Output Delivered axial displacement of the piston rod (4, 104) (in mm) |
|---|---|---|---|---|
| 1 | 1 | 15 | 15 | 0.15 |
| 2 | 2 | 10 | 15 | 0.15 |
| 3 | 3 | 7.5 | 15 | 0.15 |
| 4 | 3 | 15 | 30 | 0.3 |
| 5 | 4 | 30 | 15 | 0.15 |
| 6 | 5 | 7.5 | 15 | 0.075 |
| 7 | 6 | 10 | 15 | 0.1 |

Table 2 lists examples with different dose settings for the configurations 1-6 wherein the third column of table 2 shows the angular amount that the dose setting drum 17, 117 has been dialed. Corresponding rotational movement of the dose setting drum relative to the coupling member 25, 125 is listed in column 4 and the resulting axial displacement of the piston rod is listed in column 5.

Comparing examples 1-3 and 5 in table 2, it becomes clear that variation of the pitch of track 37, 137 changes the amount of the rotation that the dose setting member has to be dialed in order to expel a desired dose. Thereby an easy adjustment method is provided where the amount that the dose setting member has to be rotated for advancing the dose setting button one click, can be altered. Also, this provides the possibility of changing the angular distance between consecutive numbers on the dose scale. Hence, to obtain a dose scale layout with enlarged font size or, alternatively, a decreased font size, the pitch of the track 37, 137 is chosen in accordance herewith.

Comparing example 3 and 6, it is readily apparent that introducing a threaded coupling between the piston rod and the housing, i.e. making the piston rod rotatable with respect to the housing, provides for the possibility of obtaining an injection device with altered dosing amounts, e.g. a half-increment injection device.

When introducing a coupling member 25, 125 that rotates relative to the housing, the end-of-content mechanism as described above may not work in an optimal way. However, by choosing the same pitch for the additional longitudinally extending track 4b, 104b on the piston rod as for the pitch of the track 37, 137 it is ensured that the end-of-content limitation that the user may experience when setting a dose for injection, corresponds to the exact amount that will be expelled during dosing. In this way, a cartridge may be fully emptied when injecting the dose which corresponds to the end-of-content setting, i.e. the situation where the piston rod 4, 104 is fully retracted relative to the nut 13, 113, In further embodiments, the track 37, 137 may be designed to have a varying pitch along the track, i.e. having linear parts with inclined or non-inclined stretches as well as curved stretches. Also, the rotational direction of the track may be changed from one part of the track to another part of the track. One specific embodiment may be designed for larger relative dose button movements for small dose settings than for dose settings corresponding to large doses. Thereby it is ensured that the resolution for small dose settings is held at a comparative high level.

Although the above described embodiments show different specific gearbox assemblies, it is to be noted that, within the scope of the present invention, various other types of gearboxes can be used. Also, the functionality of the gearbox can be omitted while the injection device still being within the scope of the present invention.

In addition, alternative embodiments having a dose setting member which is kept axially fixed during dose setting/dosing will be applicable with the present invention and within the scope of the appended claims. One non-limiting embodiment comprises an additional slave member which is rotationally coupled to the dose setting member, and which can be used for inducing axial movement on the coupling member during dose setting.

Further, a frictional coupling may be provided instead of the above-described incremental feedback mechanism, whereby doses may be set among a continuous selection of dose amounts.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. An injection device comprising:
   a. a housing for a dose setting and injecting mechanism, the housing having a proximal end and a distal end,
   b. a rotatable dose setting member,
   c. an axially displaceable piston rod having a first thread and an additional longitudinally extending helical track,
   d. a central opening in the housing for engaging the additional longitudinally extending track of the piston rod, thus guiding the angular movement of the piston rod during axial translation of the piston rod,
   e. a threaded nut engaging the first thread of the piston rod, the nut being rotatably locked to the dose setting member during dose setting,
   f. a rotational coupling mechanism having a coupling member which is axially displaceable from a first position to a second position, the rotational coupling mechanism allowing angular movement of the nut relative to the coupling member during dose setting while preventing angular movement between the nut and the coupling member during injection,
   wherein the coupling member is angularly coupled to the housing so as to be forced to move angularly as a function of axial displacement of the coupling member relative to the housing during at least a part of the axial displacement from said first to said second position.

2. The injection device as defined in claim 1, wherein the dose setting member is axially displaceable as a result of rotation of the dose setting member relative to the housing, and that the coupling member is so coupled to the dose setting member that axial displacement of the dose setting member substantially corresponds to axial displacement of the coupling member.

3. The injection device as defined in claim 1, wherein the coupling member has a thread and is threadedly engaged with a helical thread disposed in the housing, the thread of the housing having a constant pitch.

4. The injection device as defined in claim 1, wherein the coupling member has a protrusion which mates and engages a longitudinally extending track disposed in the housing the longitudinally extending track having a variable pitch along the extension of the track.

5. The injection device as defined in claim 1, wherein the rotational coupling mechanism comprises an incremental feedback mechanism providing incremental clicks during dose setting corresponding to dose volume.

6. The injection device as defined in claim 1, wherein the injection device further comprises an injection button and a gear box assembly coupling axial movement of the injection button with axial movement of the nut.

7. The injection device as defined in claim 6, wherein the gear box assembly provides a gearing causing the nut to move a distance in the distal direction during injection that is less than the distance moved by the injection button.

8. The injection device as defined in claim 1, wherein the additional longitudinally extending track on the piston rod is helically disposed thereby forming a second thread on the piston rod.

9. The injection device as defined in claim 8, wherein the first thread and the longitudinally extending track on the piston rod are oppositely disposed.

10. The injection device as defined in claim 8, wherein the coupling member has a thread and is threadedly engaged with a helical thread disposed in the housing, the thread of the housing having a constant pitch substantially corresponding to the pitch of the additional longitudinally extending track on the piston rod.

11. The injection device as defined in claim 2, wherein the coupling member has a thread and is threadedly engaged with a helical thread disposed in the housing, the thread of the housing having a constant pitch.

12. The injection device as defined in claim 2, wherein the coupling member has a protrusion which mates and engages a longitudinally extending track disposed in the housing the longitudinally extending track having a variable pitch along the extension of the track.

13. The injection device as defined in claim 9, wherein the coupling member has a thread and is threadedly engaged with a helical thread disposed in the housing, the thread of the housing having a constant pitch substantially corresponding to the pitch of the additional longitudinally extending track on the piston rod.

14. The injection device as defined in claim 2, wherein the rotational coupling mechanism comprises an incremental feedback mechanism providing incremental clicks during dose setting corresponding to dose volume.

15. The injection device as defined in claim 3, wherein the rotational coupling mechanism comprises an incremental feedback mechanism providing incremental clicks during dose setting corresponding to dose volume.

16. The injection device as defined in claim 4, wherein the rotational coupling mechanism comprises an incremental feedback mechanism providing incremental clicks during dose setting corresponding to dose volume.

17. The injection device as defined in claim 2, wherein the injection device further comprises an injection button and a gear box assembly coupling axial movement of the injection button with axial movement of the nut.

18. The injection device as defined in claim 3, wherein the injection device further comprises an injection button and a gear box assembly coupling axial movement of the injection button with axial movement of the nut.

19. The injection device as defined in claim 4, wherein the injection device further comprises an injection button and a gear box assembly coupling axial movement of the injection button with axial movement of the nut.

20. The injection device as defined in claim 5, wherein the injection device further comprises an injection button and a gear box assembly coupling axial movement of the injection button with axial movement of the nut.

21. The injection device as defined in claim 6, wherein the injection device further comprises an injection button and a gear box assembly coupling axial movement of the injection button with axial movement of the nut.

* * * * *